United States Patent [19]

Hinnen

[11] 3,950,356

[45] Apr. 13, 1976

[54] SYNTHESIS OF PHOTOCHROMIC INDOLINESPIROPYRANS

[75] Inventor: Alain Hinnen, Vauhallan, France

[73] Assignee: Saint-Gobain Industries, Neuilly-sur-Seine, France

[22] Filed: Mar. 5, 1970

[21] Appl. No.: 16,962

[30] Foreign Application Priority Data

Mar. 6, 1969 France .............................. 69.06138

[52] U.S. Cl. .......................................... 260/326.11 S
[51] Int. Cl.$^2$ ........................................ C07D 209/54
[58] Field of Search ............... 260/326.11, 326.11 S

[56] References Cited

FOREIGN PATENTS OR APPLICATIONS 1,262,318 4/1961 France .......................... 260/326.11

OTHER PUBLICATIONS

Kittila, *Dimethylformamide Chemical Uses,* (1967), pp. VIII–IX, E. I. Du Pont de Nemours and Co.

*Primary Examiner*—Joseph A. Narcavage
*Attorney, Agent, or Firm*—Pennie & Edmonds

[57] ABSTRACT

Photochromic indolinespiropyrans are formed in a substantially pure state by the reaction of a 2-alkyleneindoline and an orthohydroxyl aromatic aldehyde dissolved in dimethylformamide.

11 Claims, No Drawings

SYNTHESIS OF PHOTOCHROMIC INDOLINESPIROPYRANS

This invention relates to a new and improved method for the production of photochromic indolinespiropyrans.

An object of this invention is to produce photochromic indolinespiropyrans which are substantially free from secondary side products and with a high yield of product.

Another object of this invention is the production of pure indolinespiropyrans in a manner whereby the product can be recovered by simple crystallization from the reaction medium.

Another object of the invention is to produce photochromic spiropyrans which do not have to be purified by successive recrystallizations.

A further object of the invention is to produce 6'-nitro-5-chloro-1,3,3-trimethylindoline-2-spiro-2'benzopyran in high yield and with a high degree of purity by a simple procedure.

A further object of the invention is to make 7'-nitro-1,3,3-trimethylindoline-2'spiro-2'-naphthopyran in substantially pure form by a simplified procedure.

A further object of the invention is to prepare indolinespiropyrans by the condensation of a 2-alkyleneindoline with an orthohydroxyl aromatic aldehyde with the elimination of water in a medium which favors the formation of the photochromic indolinespiropyran, and suppresses the formation of secondary products, and from which the indolinespiropyran can be recovered by crystallization.

A further object of the invention is an improved method for the condensation of salicylaldehydes with 2-alkyleneindolines.

A still further object of this invention is the condensation of an orthohydroxylnaphthaldehyde with a 2-methylene-indoline in an improved manner.

The production of photochromic indolinespiropyrans by the condensation of orthohydroxyl aromatic aldehydes with 2-alkyleneindolines is known. The prior art teaches that a number of orthohydroxy aromatic aldehydes, such as the salicylaldehydes, o-vanillin, and the naphthylaldehydes with substitutions on the ring can be used to prepare indolinespiropyrans. While 1,3,3-trimethyl-2-methyleneindoline, also known as Fischer's base has been commonly used, other alkylene indolines having other than methyl groups on the indoline ring and substitutions on the aromatic ring have been known. In the prior art the condensation has been conducted with the components dissolved in an alcohol.

The invention is based upon the applicant's discovery that the alcohols used as the reaction medium in the prior art contribute to the formation of undesired secondary products and cause low yields of the desired products. The applicant found that if the condensation takes place in a more favorable medium the secondary products are not formed and there is a much higher yield or product. The medium should be one with a high degree of solvency for the aldehyde so that more concentrated reaction can occur. The applicant found that dimethylformamide is a most desirable reaction medium, as it results in a very high yield of product and offers an easy mode of recovering the pure product. Dimethylformamide is frequently designated by the abbreviation "D.M.F.".

The applicant found that the aliphatic alcohols are not good mediums for obtaining a favorable synthesis of the indolinespiropyrans, and that this was due to at least two reasons:

1. The desired indolinespiropyran is often contaminated with a quantity of the acetal of the hydroxyl aromatic aldehyde. This secondary product is undesirable and can be separated from the indolinespiropyran only by dissolving the product and by recrystallization successively for a number of times. This procedure diminishes the recovery of the product and complicates the procedure.

2. In some cases the reaction in an alcoholic medium results in the formation of a secondary product in which another molecule of the methylene indoline is attached to the pyran group forming a dihydropyran. This formation of the secondary compound is disclosed in the article by Koelsch et al. in The Journal of the American Chemical Society, Vol. 74, pages 6288 and 6289, 1953. This structure has also been redetermined by A. Hinnen, C. Audic and R. Gautron (Bull. Soc. Chim 1968 page 2066).

The relative proportions of the desired indolinespiropyran and the secondary products obtained from an alcoholic bath are dependent upon the temperature and the time of condensation reaction among other factors.

In many of the prior art processes it was found that the amount of the secondary products produced exceeds the amount of the desired product. This was particularly the case in the preparation of 8'methoxy-6'-nitro-1,3,3,-trimethylindoline-2-spiro-2'-benzopyran as shown by Koelsch et al. This results in very low yields of the desired product with the necessity for purification by successive recrystallizations, which is a time consuming and painstaking operation.

However, on the contrary when the reaction is conducted in dimethylformamide, in accordance with the present invention, the formation of the acetal and the dihydropyran and other secondary products is avoided and the formation of the desired indolinespiropyran is encouraged. The dimethylformamide is an excellent solvent for the orthohydroxyl aromatic aldehydes and thus the concentration of the reactants in the solution can be increased beyond that which is possible when using poorer solvents, such as the alcohols. The higher concentration of reactants in the dimethylformamide permits the use of smaller reaction vessels and permits the reduction in time of reaction. In the prior art, using the alcoholic medium the condensation required several hours, while in the present invention using D.M.F. the condensation can be carried to completion in fifteen minutes.

The applicant has proven that when substantially pure starting materials are dissolved in D.M.F. the reaction can be carried to completion in fifteen minutes and the substantially pure indolinespiropyran separated from the medium, by cooling or adding a nonsolvent, without the need for recrystallization. The use of D.M.F. as solvent thus permits the recovery of more product directly from the reaction medium with substantially the same purity as was formerly obtained only by numerous recrystallizations.

The following examples are not to be considered as limiting, since any of the well known substituted indolines or aldehydes can be used in a similar manner. The examples compare the preparation with the same reactants in an alcoholic medium in accordance with the best practice of the prior art, with the preparation from the same reactants in solution in D.M.F. for the formation of photochromic indolinespiropyrans.

EXAMPLE I

Preparation of
6'nitro-5-chloro-1,3,3,-trimethyl-indoline-2-spiro-2'-benzopyran.

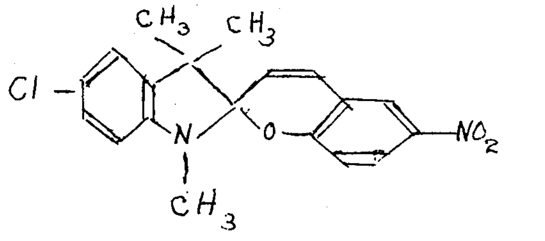

from 5-nitrosalicylaldehyde

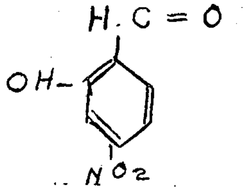

and 5 chloro-1,3,3-trimethyl 2 methylene indoline

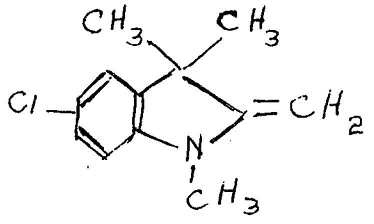

Comparative test a. In an alcoholic solution

A mixture of 1.67 g. of 5 nitrosalicylaldehyde and 2.07 g. of 5-chloro-1,3,3 trimethyl-2-methyleneindoline in 20 $cm^3$ of ethanol is heated under reflux for two hours. The mixture is then cooled to 0° C. and the precipitate is recovered by filtering and then drying. The product contains about 20% of the secondary product, the dihydropyran. The compound is purified by four recrystallizations from benzene.

The purified product recovered amounted to 1.2 g. representing a recovery of 34% of theoretical, and had a melting point of 155° C.

Present process b. In dimethylformamide

In accordance with the invention 1.67 g. of 5-nitrosalicylaldehyde is dissolved in 4 $cm^3$ of dimethyl formamide and 2.07 g. of 5-chloro-1,3,3-trimethyl-2-methyleneindoline is added, and is heated under reflux for fifteen minutes. The composition 6'nitro-5 chloro-1,3,3-trimethylindoline-2-spiro-2'-benzopyran is very soluble in D.M.F. and is not precipitated by simple cooling. The compound is precipitated by adding 60 $cm^3$ of ethanol. The precipitate is filtered and is dried. The dry precipitate weighs 2.9 g. and is a pure product having a melting point of 155° C. The recovery is 81%.

The product has an infra-red spectrum which is exactly superposable on the spectrum of the indolinespiropyran prepared in an alcoholic medium and then purified by six successive crystallizations. The absence of all emission of fluorescence proves the absence of impurities such as the dihydropyrans.

EXAMPLE II

Preparation of
7'nitro-1,3,3-trimethylindoline-2-spiro-2'-naphthopyran.

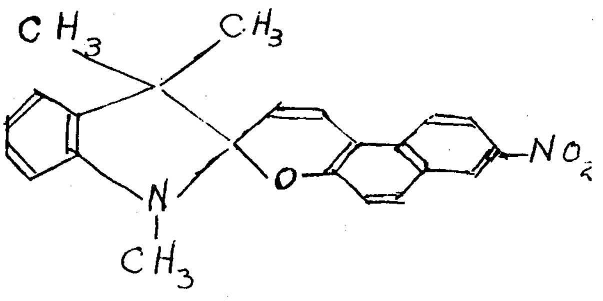

from 2-hydroxy-6-nitronaphthaldehyde

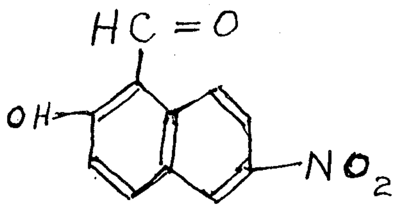

and 1,3,5-trimethyl-2-methyleneindoline

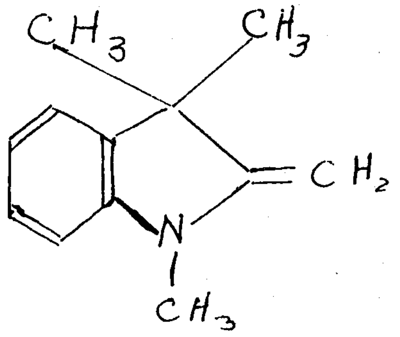

Comparative test a. In alcoholic solution

A solution is prepared of 2.17 g. (0.0295 mole) of 2-hydroxy-6-nitro-1-naphthaldehyde in 80 $cm^3$ of hot ethanol, to this is added 1.73 g. (0.0295 mole) of 1,3,3-trimethyl-2-methyleneindoline and the mixture is heated for two hours at boiling temperature under reflux. The mixture is then cooled to 0° C. and a precipitate of indolinespiropyran is obtained. This is filtered and dried. The composition has a melting point of 234° C. The product is recrystallized twice from benzene and the melting point is increased to 240°–241° C. The purified product weight is 1.34 g. which represents a recovery of 36%.

Present invention b. In dimethylformamide solution 6.4 g. (0.0295 mole) of 2-hydroxy-6-nitro-1-naphthaldehyde is dissolved in 50 $cm^3$ of dimethylformamide. 5.11 g. (0.0295 mole) of 1,3,3-trimethyl-2-methyleneindoline is added and heated under reflux for fifteen minutes. The solution is cooled to 10° C. and the precipitate is filtered and is dried under vacuum. The product 7'nitro-1,3,3-trimethylindoline-2-spiro-2'-naphthopyran has a fusion point of 240° C. and weighs 10.0 g. representing a recovery of 91%.

The infrared spectrum of the product is exactly superposable over the spectrum of the product obtained by reaction in an alcoholic medium after it has been purified by four recrystallizations in benzene.

These comparative examples show that the present process of conducting the reaction in D.M.F. has great advantages over the prior art in which the condensation is conducted in an alcoholic medium, in that the time is reduced, the volume of medium is less, the quantity of product is more than twice that recovered by the prior process and that the purity of the product recovered by simple precipitation from the D.M.F. is equal to that of the prior art after having been recrystallized for a number of times. The present process offers a practical way to produce these photochromic indolinespiropyrans at a much lower cost.

I claim:

1. A method for the synthesis of photochromic indolinespiropyrans by the condensation of a base of an alkylene-2-indoline and an orthohydroxyl-aromatic aldehyde, which comprises dissolving the aromatic aldehyde in dimethyl formamide, adding the indoline base to the solution and heating under reflux, and recovering the photochromic indolinespiropyran.

2. A method according to claim 1 in which the indolinespiropyran is recovered by crystallization from the dimethylformamide.

3. A method according to claim 1 in which the indolinespiropyran is recovered by the addition of an alcohol to the dimethylformamide solution.

4. A method according to claim 1 in which the indoline base is 1,3,3-trimethyl-2-methyleneindoline.

5. A method according to claim 1 in which the indoline base is 5-chloro-1,3,3-trimethyl-2-methyleneindoline.

6. A method according to claim 1 in which the orthohydroxyl aromatic aldehyde is a salicylaldehyde.

7. A method according to claim 1 in which the orthohydroxyl aromatic aldehyde is 5 nitrosalicylaldehyde.

8. A method according to claim 1 in which the orthohydroxyl aldehyde is a 2 hydroxyl 1 naphthaldehyde.

9. A method according to claim 8 in which the orthohydroxyl aromatic aldehyde is 2-hydroxyl-6-nitro-1-naphthaldehyde.

10. A method for the preparation of 6'-nitro-5-chloro-1,3,3-trimethyl-indoline-2-spiro-2'-benzopyran which comprises dissolving 5-nitrosalicylaldehyde in dimethylformamide, adding 5-chloro-1,3,3-trimethyl-2-methyleneindoline and heating under reflux.

11. A method for the preparation of 7'-nitro-1,3,3-indoline-2-spiro-2'-naphthopyran, which comprises dissolving 2-dihydroxy-6-nitro-1-naphthaldehyde in dimethylformamide, adding 1,3,3-trimethyl-2-methyleneindoline, and refluxing the mixture.

* * * * *